(12) United States Patent
Staller et al.

(10) Patent No.: US 10,705,067 B2
(45) Date of Patent: Jul. 7, 2020

(54) METHODS AND SYSTEMS FOR TESTING PERFORMANCE OF A CATALYST ELEMENT

(71) Applicant: EmeraChem, LLC, Knoxville, TN (US)

(72) Inventors: Tracy D. Staller, Seymour, TN (US); Steven G. DeCicco, Knoxville, TN (US); Lisa D. Mitchell, Clinton, TN (US); David Matthew Loy, Lenoir City, TN (US); Tom Sughrue, Knoxville, TN (US)

(73) Assignee: Miratech Knoxville, LLC, Knoxville, TN (US)

( * ) Notice: Subject to any disclaimer, the term of this patent is extended or adjusted under 35 U.S.C. 154(b) by 235 days.

(21) Appl. No.: 15/717,575

(22) Filed: Sep. 27, 2017

(65) Prior Publication Data

US 2018/0095063 A1 Apr. 5, 2018

Related U.S. Application Data

(60) Provisional application No. 62/402,804, filed on Sep. 30, 2016.

(51) Int. Cl.
*G01N 33/22* (2006.01)

(52) U.S. Cl.
CPC ................... *G01N 33/225* (2013.01)

(58) Field of Classification Search
CPC ..................................... G01N 33/225
USPC ........................................ 73/23.31
See application file for complete search history.

(56) References Cited

U.S. PATENT DOCUMENTS 9,068,954 B1    6/2015  Robinson, Jr. et al.
9,562,880 B1 *  2/2017  Robinson, Jr. ......... G01N 31/10

* cited by examiner

*Primary Examiner* — Tarun Sinha
(74) *Attorney, Agent, or Firm* — Rudy J. Ng; Bozicevic, Field & Francis LLP

(57) ABSTRACT

Methods and systems for testing performance of a catalyst element are provided. The catalyst element can be an oxidation catalyst element or a non-selective catalytic reduction catalyst element, where the subject methods and systems are configured for testing under various lambda ($\lambda$) conditions. The subject methods and systems find use in a variety of applications where it is desired to test the performance of a catalyst element.

26 Claims, 6 Drawing Sheets

Table 1

| Catalyst ID | Type | Status | Source | NOx (ppmv) | CO (ppmv) | O2 (%) | lambda | NOx DRE | CO DRE |
|---|---|---|---|---|---|---|---|---|---|
| Cat 1 | NSCR | Degreened | inlet | 1284 | 682 | 0.33 | 0.992 | | |
| | | | outlet | 38 | 344 | 0 | 0.992 | 97.04% | 49.56% |
| Cat 2 | NSCR | Degreened | inlet | 1360 | 690 | 0.32 | 0.993 | | |
| | | | outlet | 63 | 129 | 0.015 | 0.992 | 95.37% | 81.30% |
| Cat 3 | NSCR | Degreened | inlet | 1368 | 660 | 0.33 | 0.992 | | |
| | | | outlet | 57 | 165 | | | 95.83% | 75.00% |
| Cat 4 | NSCR | Field Aged | inlet | 1375 | 556 | 0.29 | 0.992 | | |
| | | | outlet | 181 | 574.28 | 0.04 | 0.992 | 86.84% | -3.29% |
| Cat 5 | NSCR | Field Aged | inlet | 1347 | 699 | 0.315 | 0.992 | | |
| | | | outlet | 490 | 555 | 0.11 | 0.992 | 63.62% | 20.60% |
| Cat 6 | NSCR | Field Aged | inlet | 1321 | 848 | 0.32 | 0.992 | | |
| | | | outlet | 899 | 808 | 0.185 | 0.992 | 31.95% | 4.72% |
| Cat 7 | NSCR | RECLAIM | inlet | 1329 | 603 | 0.3 | 0.992 | | |
| | | | outlet | 1096 | 511 | | 0.992 | 17.53% | 15.26% |

FIG. 6

Table 2

| Catalyst ID | Type | Status | Source | CO (ppmv) | CO DRE |
|---|---|---|---|---|---|
| Cat 8 | Oxidation | Degreened | inlet | 888 | |
| | | | outlet | 63.2 | 92.88% |
| Cat 9 | Oxidation | Field Aged | inlet | 697 | |
| | | | outlet | 134 | 80.77% |
| Cat 10 | Oxidation | Field Aged | inlet | 696 | |
| | | | outlet | 248 | 64.37% |
| Cat 11 | Oxidation | Field Aged | Inlet | 646.42 | |
| | | | outlet | 73 | 88.71% |

FIG. 7

METHODS AND SYSTEMS FOR TESTING PERFORMANCE OF A CATALYST ELEMENT

CROSS-REFERENCE TO RELATED APPLICATIONS

This application claims priority pursuant to 35 U.S.C. § 119(e) to the filing date of U.S. Provisional Patent Application Ser. No. 62/402,804, filed Sep. 30, 2016, the disclosure of which is herein incorporated by reference.

INTRODUCTION

Periodic testing of the performance of a catalyst, such as for example an emissions catalyst, is of interest in industrial applications to ensure that the catalyst is performing within acceptable parameters. For example, the activity of a catalyst for removing undesirable air pollutants from engine exhaust can be tested. These test results can be analyzed to determine if the emissions catalyst is achieving a reduction in the emissions of air pollutants that meet threshold levels required by local rules, regulations and/or permits.

One common method for testing the performance of an emissions catalyst element involves removing a portion of the catalyst element and testing that portion of the catalyst element to determine the overall activity of the catalyst. However, this method may lead to inaccuracies in the results because removing a portion of the catalyst element often damages the catalyst coating. Inaccuracies could also result if the activity of the catalyst element varies from one area of the catalyst element to another area. In addition, because one or more portions of the catalyst element are removed for testing, this may cause leakage or may be detrimental to the performance of the catalyst element as a whole.

Accordingly, there is interest in developing non-destructive methods and systems for testing of the performance of an emissions catalyst that are amenable to various different catalyst sizes, shapes, and types.

SUMMARY

Methods and systems for testing performance of a catalyst element are provided. The catalyst element can be an oxidation catalyst element or a non-selective catalytic reduction catalyst element, where the subject methods and systems are configured for testing under various lambda ($\lambda$) conditions. The subject methods and systems find use in a variety of applications where it is desired to test the performance of a catalyst element.

Aspects of the present disclosure include a method for testing performance of an oxidation catalyst element or a non-selective catalytic reduction catalyst element. The method includes: mounting a catalyst element in a gas flow path of a system that includes a gas inlet upstream from the catalyst element and a gas outlet downstream from the catalyst element; introducing a predetermined amount of one or more reagent gases into a carrier gas to produce a test gas flowing through the gas flow path of the gas inlet; measuring an inlet concentration of the one or more reagent gases in the test gas in the gas flow path of the gas inlet; measuring an outlet concentration the one or more reagent gases in the test gas in the gas flow path of the gas outlet; and determining the performance of the catalyst element based on the measured inlet concentration of the one or more reagent gases and the measured outlet concentration of the one or more reagent gases. For the oxidation catalyst element, the one or more reagent gases include one or more reductant gases, and the test gas flowing into the emissions catalyst element has a lambda ($\lambda$) value of greater than 1. For the non-selective catalytic reduction catalyst element, the one or more reagent gases include one or more reductant gases and one or more oxidant gases, and the test gas flowing into the catalyst element has a $\lambda$ value of 1 or less including oxygen present in the test gas.

In some embodiments, the reductant gas includes carbon monoxide, gaseous aliphatic hydrocarbons, gaseous olefinic hydrocarbons, hydrogen, or mixtures thereof.

In some embodiments, the oxidant gas includes nitric oxide, nitrogen dioxide, oxygen, or mixtures thereof.

In some embodiments, the carrier gas flowing through the gas flow path for a $\lambda$ value greater than 1 includes air.

In some embodiments, the carrier gas flowing through the gas flow path for a $\lambda$ value of 1 or less is an inert gas, such as nitrogen, carbon dioxide, argon, and the like, or combinations thereof.

In some embodiments, the test gas also includes water vapor.

In some embodiments, the test gas flowing through the gas flow path for a $\lambda$ value of 1 or less includes oxygen.

In some embodiments, the test gas includes carbon monoxide in a predetermined concentration ranging from 10 ppmv to 10,000 ppmv and a $\lambda$ value greater than 1.

In some embodiments, the test gas includes one or more hydrocarbons in a predetermined concentration ranging from 10 ppmv to 10,000 ppmv and a $\lambda$ value greater than 1.

In some embodiments, the test gas includes an oxidant gas (e.g., nitrogen oxides, NOx) in a predetermined concentration ranging from 20 ppmv to 20,000 ppmv, and a reductant gas of a concentration to yield a $\lambda$ value of 1 or less.

In some embodiments, the method includes heating the carrier gas in the gas flow path before introducing the reagent gas into the carrier gas.

In some embodiments, the method includes heating the reagent gas, the carrier gas, the test gas, or combinations thereof.

In some embodiments, the method also includes mixing the reagent gas with the carrier gas to produce the test gas.

In some embodiments, the test gas in the gas flow path at the gas inlet has a temperature ranging from 212° F. (100° C.) to 1100° F. (593° C.).

In some embodiments, the test gas flowing through the gas flow path has a flow rate ranging from 0.5 SCFM to 20 SCFM.

In some embodiments, the method includes quantitatively determining the performance of the catalyst element in real time.

In some embodiments, the method includes determining the performance of the catalyst element at two or more distinct regions of the catalyst element.

Aspects of the present disclosure also include a system for testing performance of an oxidation catalyst element or a non-selective catalytic reduction catalyst element. The system includes a gas source that provides a flow of a carrier gas through the system; a gas inlet to a catalyst element that seals against an upstream surface of the catalyst element; a gas outlet from the catalyst element that seals against a downstream surface of the catalyst element; a detector that measures a concentration of one or more reagent gases in a test gas upstream from the gas inlet or measures a concentration of the one or more reagent gases in the test gas downstream from the gas outlet; and a processor that determines the performance of the catalyst element based on the measured inlet concentration of the one or more reagent gases and measured outlet concentration of the one or more reagent gases. For the oxidation catalyst element, the one or more reagent gases include one or more reductant gases, and the test gas flowing into the catalyst element has a λ value of greater than 1. For the non-selective catalytic reduction catalyst element, the one or more reagent gases include one or more reductant gases and one or more oxidant gases, and the test gas flowing into the catalyst element has a λ value of 1 or less including oxygen present in the test gas. In embodiments of the presently disclosed system, the cross sectional area of the gas inlet is less than the cross sectional area of the gas outlet.

In some embodiments, the reductant gas includes carbon monoxide, gaseous aliphatic hydrocarbons, gaseous olefinic hydrocarbons, hydrogen, or mixtures thereof.

In some embodiments, the oxidant gas includes nitric oxide, nitrogen dioxide, oxygen, or mixtures thereof.

In some embodiments, the system also includes a gas controller that provides a predetermined quantity of the carrier gas flowing through the system.

In some embodiments, the gas controller provides a predetermined quantity of the reagent gas to the carrier gas flowing through the system.

In some embodiments, the system also includes one or more heaters that heats the carrier gas, the reagent gas, the test gas, or combinations thereof, flowing through the system.

In embodiments of the presently disclosed system, the gas inlet has a diameter less than a dimension of the catalyst element such that the gas inlet seals against a portion of the upstream surface of the catalyst element, and the gas outlet has a diameter less than a dimension of the catalyst element such that the gas outlet seals against a portion of the downstream surface of the catalyst element.

In some embodiments, the carrier gas flowing through the system for a λ value greater than 1 includes air.

In some embodiments, the carrier gas flowing through the system for a λ value of 1 or less includes an inert gas.

In some embodiments, the test gas also includes water vapor.

In some embodiments, the test gas flowing through the gas flow path for a λ value of 1 or less includes oxygen.

BRIEF DESCRIPTION OF THE FIGURES

FIG. 6 shows Table 1, which shows the results of the tests from Example 3.

FIG. 7 shows Table 2, which shows the results of the tests from Example 4.

DETAILED DESCRIPTION

Figure 1:
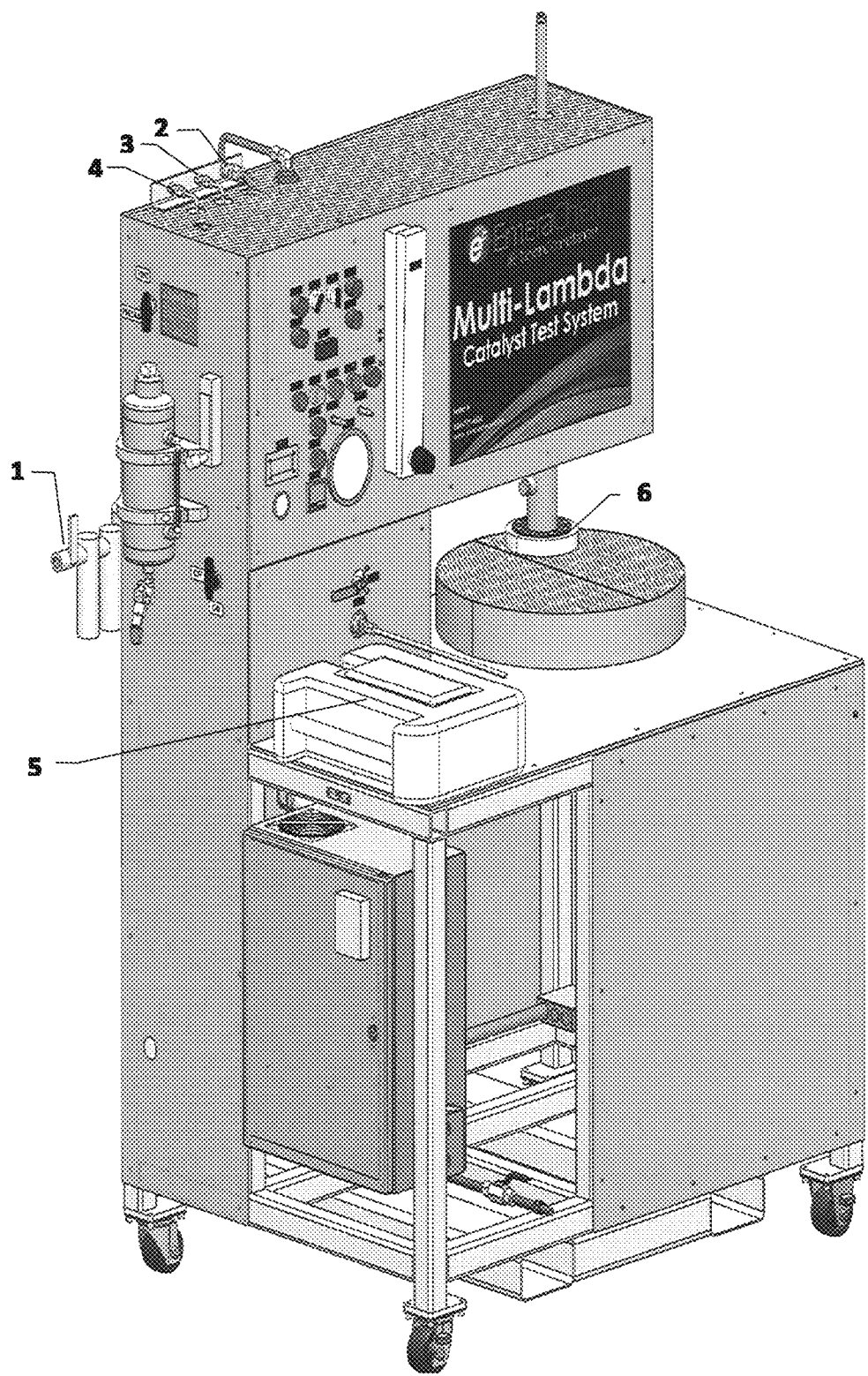
FIG. 1 shows an image of a system for testing the performance of a catalyst element, according to embodiments of the present disclosure.

Methods and systems for testing performance of a catalyst element are provided. The catalyst element can be an oxidation catalyst element or a non-selective catalytic reduction catalyst element, where the subject methods and systems are configured for testing under various lambda (λ) conditions. The subject methods and systems find use in a variety of applications where it is desired to test the performance of an catalyst element.

Before the present invention is described in greater detail, it is to be understood that this invention is not limited to the particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

In further describing the subject invention, embodiments of the subject methods are described first in greater detail, followed by a review of embodiments of systems in which the subject methods find use.

Methods

Provided are methods for testing performance of a catalyst element, such as but not limited to an emissions catalyst element. In some instances, the catalyst element is an emissions catalyst element, such as an oxidation emissions catalyst element or a non-selective catalytic reduction (NSCR) emissions catalyst element. The subject methods and systems are configured for testing under various lambda ($\lambda$) conditions. As used herein "lambda" or "$\lambda$" refers to the stoichiometric ratio of oxidants to reductants in a gas stream on an oxygen basis.

In general, aspects of embodiments of the presently disclosed methods include one or more steps associated with testing the performance of a catalyst element, such as an emissions catalyst element. In some instances, the method includes mounting a catalyst element (e.g., the emissions catalyst element to be tested) in a gas flow path of a system. As described in more detail herein, the system can be configured to perform the presently disclosed methods for testing catalyst performance. For instance, the system may include various components to direct the flow of a gas thorough the system and through the catalyst element to be tested. The system includes a gas inlet upstream from the catalyst element and a gas outlet downstream from the catalyst element. By "upstream" is meant positioned proximal to (i.e., closer to) a source of a gas flow stream flowing through the gas flow path of the system. By "downstream" is meant positioned distal to (i.e., further away from) the source of a gas flow stream flowing through the gas flow path of the system.

In embodiments of the present disclosure, mounting the catalyst element in the gas flow path of the system includes positioning the catalyst element between the gas inlet and the gas outlet of the system. For example, at least a portion of the catalyst element may be positioned between the gas inlet and the gas outlet of the system. In certain instances, the portion of the catalyst element that is tested may be the entire catalyst element (i.e., 100% of the area of the catalyst element). In other cases, the portion of the catalyst element that is tested is less than the entire area of the whole catalyst element. For instance, the portion of the catalyst element that is tested may be 95% or less of the entire area of the whole catalyst element, such as 90% or less, or 85% or less, or 80% or less, or 75% or less, or 70% or less, or 65% or less, or 60% or less, or 55% or less, or 50% or less, or 45% or less, or 40% or less, or 35% or less, or 30% or less, or 25% or less, or 20% or less, or 15% or less, or 10% or less, or 5% or less of the entire area of the whole catalyst element. In these instances, one or more different portions of the catalyst element may be tested, such as 2 or more portions, or 3 or more portions, or 4 or more portions, or 5 or more portions, or 6 or more portions, or 7 or more portions, or 8 or more portions, or 9 or more portions, or 10 or more portions. Thus, the method may include determining the performance of the catalyst element at two or more distinct regions of the catalyst element. As such, in some instances, the method includes repeating the test method 2 or more times at distinct regions of the catalyst element. The results from the testing of 2 or more portions of the catalyst element can be averaged together to provide an indication of the average performance of the entire catalyst element. By "average" is meant the arithmetic mean.

In addition, mounting the catalyst element in the gas flow path of the system includes contacting the gas inlet to a surface of the catalyst element. For instance, the gas inlet may be contacted to a surface of the catalyst element where gas flowing through the gas inlet enters into the catalyst element. In some cases, the gas inlet is contacted to a portion of the upstream surface of the catalyst element. By "upstream surface" is meant the surface of the catalyst element positioned proximal to (i.e., closer to) a source of a gas flow stream flowing through the gas flow path of the system. As described above, the portion of the upstream surface of the catalyst element contacted with the gas inlet can be the entire area of the whole catalyst element, or less than the entire area of the whole catalyst element.

Similarly, mounting the catalyst element in the gas flow path of the system can include contacting the gas outlet to a surface of the catalyst element. For instance, the gas outlet may be contacted to a surface of the catalyst element where gas flowing through the catalyst element exits the catalyst element. In some cases, the gas outlet is contacted to a portion of the downstream surface of the catalyst element. By "downstream surface" is meant the surface of the catalyst element positioned distal to (i.e., further away from) the source of a gas flow stream flowing through the gas flow path of the system. As described above, the portion of the downstream surface of the catalyst element contacted with the gas outlet can be the entire area of the whole catalyst element, or less than the entire area of the whole catalyst element, where the cross sectional area of the gas inlet is less than the cross sectional area of the gas outlet.

In some cases, the catalyst element is mounted in the system in a substantially horizontal orientation (i.e., where the gas flow path of the system flows substantially vertically through the catalyst element). In these cases, mounting the catalyst element in the system may include raising and/or lowering one or both of the gas inlet and the gas outlet such that the gas inlet and the gas outlet contact their respective surfaces of the catalyst element. In other cases, the catalyst element may be mounted in the system in a substantially vertical orientation (i.e., where the gas flow path of the system flows substantially horizontally through the catalyst element). In these cases, mounting the catalyst element in the system may include moving one or both of the gas inlet and the gas outlet in a lateral (horizontal) direction such that the gas inlet and the gas outlet contact their respective surfaces of the catalyst element.

In certain instances, mounting the catalyst element in the system also includes positioning one or more gaskets between the upstream surface of the catalyst element and the gas inlet of the system and/or positioning one or more gaskets between the downstream surface of the catalyst element and the gas outlet of the system. In some cases, the use of one or more gaskets facilitates forming a gas-tight seal between the surface of the catalyst element and the gas inlet and/or gas outlet of the system.

In certain embodiments, mounting the catalyst element in the system may include applying a pressure on the surface of the catalyst element with the gas inlet and/or gas outlet. For example, as the gas inlet and/or gas outlet is raised or lowered (or moved laterally) towards the surface of the catalyst element, the gas inlet and/or gas outlet may contact the surface of the catalyst element and apply a pressure on the surface of the catalyst element (or on the gasket positioned between the surface of the catalyst element and the gas inlet and/or gas outlet). In some cases, applying a pressure on the surface of the catalyst element facilitates forming a gas-tight seal between the surface of the catalyst element and the gas inlet and/or gas outlet of the system, or between the gasket positioned between the surface of the catalyst element and the gas inlet and/or gas outlet.

Once the catalyst element is satisfactorily mounted in the system, the performance of the catalyst element can be tested. In some instances, the method includes preheating the catalyst element prior to testing the performance of the catalyst element. For example, the method may include preheating the catalyst element to a temperature ranging from 212° F. (100° C.) to 1500° F. (815° C.), such as from 300° F. (150° C.) to 1400° F. (760° C.), or from 400° F. (205° C.) to 1300° F. (705° C.), or from 500° F. (260° C.) to 1200° F. (650° C.), or from 500° F. (260° C.) to 1100° F. (590° C.), or from 500° F. (260° C.) to 1000° F. (540° C.). In some cases, the catalyst element is heated to a temperature ranging from 212° F. (100° C.) to 1100° F. (590° C.). In some cases, preheating the catalyst element includes contacting the catalyst element (or a portion thereof) with a flow of a heated gas. For instance, the catalyst element may be contacted with a flow of heated air.

In certain embodiments, testing the performance of the catalyst element includes introducing a flow of a carrier gas through the catalyst element (or a portion thereof). In some cases, the method includes flowing a carrier gas through the gas flow path of the system, such as flowing a carrier gas through the gas flow path of the gas inlet and into the catalyst element. The carrier gas may be any convenient carrier gas. In some cases, the carrier gas is an inert gas that is substantially non-reactive with respect to the catalyst element and the catalysts contained therein. Examples of inert gases include, but are not limited to, nitrogen, carbon dioxide, argon, and the like, and combinations thereof. In other cases, the carrier gas can include one or more gases that participate in reactions catalyzed by the catalyst element. For example, the carrier gas may include oxygen, water vapor, and the like, or combinations thereof. In some instances, the carrier gas is air. In some cases, the carrier gas is nitrogen. Mixtures of carrier gases may also be used. In some instances, the carrier gas is heated to a temperature range described above prior to contacting the carrier gas to the catalyst element. In some instances, the carrier gas is heated to a temperature range described above prior to introducing a reagent gas into the carrier gas, as described in more detail below. For instance, the carrier gas may be heated to a temperature ranging from 212° F. (100° C.) to 1500° F. (815° C.), such as from 300° F. (150° C.) to 1400° F. (760° C.), or from 400° F. (205° C.) to 1300° F. (705° C.), or from 500° F. (260° C.) to 1200° F. (650° C.), or from 500° F. (260° C.) to 1100° F. (590° C.), or from 500° F. (260° C.) to 1000° F. (540° C.). In some cases, the carrier gas is heated to a temperature ranging from 212° F. (100° C.) to 1100° F. (590° C.). In certain embodiments, the carrier gas flowing through the gas flow path has a flow rate ranging from 0.1 SCFM to 50 SCFM, such as from 0.5 SCFM to 45 SCFM, or from 0.5 SCFM to 40 SCFM, or from 0.5 SCFM to 35 SCFM, or from 0.5 SCFM to 30 SCFM, or from 0.5 SCFM to 25 SCFM, or from 0.5 SCFM to 20 SCFM, or from 0.5 SCFM to 15 SCFM, or from 0.5 SCFM to 10 SCFM. For example, the carrier gas flowing through the gas flow path has a flow rate ranging from 0.5 SCFM to 20 SCFM.

In certain embodiments, testing the performance of the catalyst element includes introducing a predetermined quantity of a reagent gas into the carrier gas to produce a test gas flowing through the gas flow path of the system. For example, the reagent gas may be introduced into the carrier gas flowing through the gas flow path of the gas inlet, such that the reagent gas contacts the catalyst element (or portion thereof). In some cases, the method includes mixing the reagent gas with the carrier gas to produce the test gas. In certain cases, the test gas is heated to a temperature range described above. For instance, the test gas may be heated to a temperature ranging from 212° F. (100° C.) to 1500° F. (815° C.), such as from 300° F. (150° C.) to 1400° F. (760° C.), or from 400° F. (205° C.) to 1300° F. (705° C.), or from 500° F. (260° C.) to 1200° F. (650° C.), or from 500° F. (260° C.) to 1100° F. (590° C.), or from 500° F. (260° C.) to 1000° F. (540° C.). In some cases, the test gas is heated to a temperature ranging from 212° F. (100° C.) to 1100° F. (590° C.). In certain embodiments, the test gas flowing through the gas flow path has a flow rate ranging from 0.1 SCFM to 50 SCFM, such as from 0.5 SCFM to 45 SCFM, or from 0.5 SCFM to 40 SCFM, or from 0.5 SCFM to 35 SCFM, or from 0.5 SCFM to 30 SCFM, or from 0.5 SCFM to 25 SCFM, or from 0.5 SCFM to 20 SCFM, or from 0.5 SCFM to 15 SCFM, or from 0.5 SCFM to 10 SCFM. For example, the test gas flowing through the gas flow path has a flow rate ranging from 0.5 SCFM to 20 SCFM.

If the temperature of the catalyst element, the carrier gas, the reagent gas, or the test gas that includes the carrier gas and reagent gas is outside the desired temperature range, the method may include adjusting the temperature of the catalyst element, the carrier gas, the reagent gas, or the test gas. In some cases, this can be achieved by adjusting the temperature of the carrier gas and contacting the carrier gas with the catalyst element and/or mixing the carrier gas with the reagent gas to produce the test gas. For example, if the temperature of the gas stream upstream from the catalyst element is greater than a desired temperature or temperature range, then the adjusting may include reducing the temperature of the gaseous stream to the desired temperature or temperature range. In some cases, reducing the temperature of the gas stream may include, but is not limited to, reducing the temperature of a heater that is heating the gas stream. If the temperature of the gas stream upstream from the catalyst element is lower than the desired temperature or temperature range, then the adjusting may include increasing the temperature of the gas stream to the desired temperature or temperature range. For example, increasing the temperature of the gas stream may include, but is not limited to, increasing the temperature of a heater that is heating the gas stream. Thus, in some instances, the method includes measuring the temperature of the carrier gas, the reagent gas, and/or the test gas upstream from the catalyst element, and adjusting the temperature of the carrier gas, the reagent gas, and/or the test gas to be within a desired temperature range.

The test gas may be any convenient gas used for testing the performance of a catalyst element, such as but not limited to an emissions catalyst element. For example, the test gas may include one or more gases typically produced by a combustion source, such as an engine (e.g., a combustion engine, a reciprocating engine, a reciprocating internal combustion engine, a turbine, etc.), a boiler (e.g., a utility boiler, an industrial boiler, etc.), and the like. In some cases, the test gas may include one or more gases produced by a combustion engine, such as flue gas emissions from a power plant. In some instances, the test gas includes one or more gases that participate in reactions catalyzed by the catalyst(s) contained in the emissions catalyst element.

In other embodiments, the method may be used for testing the performance of a catalyst element other than an emissions catalyst element. For example, any type of catalyst element used for catalysis of gas phase reactions (e.g., oxidation or reduction reactions, or any other type of gas phase reactions) can be tested using the methods and systems of the present disclosure. Examples include, but are not limited to, oxidation or reduction catalyst elements, such as catalyst elements used in pharmaceutical research, pharmaceutical manufacturing, academic research, and the like.

In certain embodiments, the composition of the test gas depends on the type of catalyst element that is being tested. As such, in certain embodiments, the method includes determining the type of catalyst element that is to be tested. For example, the catalyst element can be an oxidation emissions catalyst element or a non-selective catalytic reduction (NSCR) emissions catalyst element.

In some instances, the method is configured for testing the performance of an oxidation catalyst element. For the oxidation catalyst element, the test gas may include one or more reductant gases. Stated another way, for an oxidation catalyst element, the reagent gas may be one or more reductant gases. The reductant gas may be oxidized in an oxidation reaction catalyzed by the oxidation catalyst element. Examples of suitable reductant gases include, but are not limited to, carbon monoxide, gaseous aliphatic hydrocarbons (e.g., methane, ethane, propane, butane, etc.), gaseous olefinic hydrocarbons (e.g., ethene, propene, and butene, etc.), hydrogen, or mixtures thereof. One or more reductant gases may be used in the methods and systems described herein to test the performance of a catalyst element.

In certain embodiments of the methods for testing the performance of an oxidation catalyst element, the test gas flowing into the emissions catalyst element has a lambda ($\lambda$) value of greater than 1. As described above, "lambda" or "$\lambda$" refers to the stoichiometric ratio of oxidants to reductants in a gas stream on an oxygen basis. For example, for an oxidation catalyst element, the lambda value ($\lambda$ value) can be greater than 1, such as 2 or more, or 3 or more, or 4 or more, or 5 or more, or 6 or more, or 7 or more, or 8 or more, or 9 or more, or 10 or more, or 15 or more.

In certain embodiments, the test gas for an oxidation catalyst element includes one or more reductant gases, such as carbon monoxide. For instance, the reagent gas can be carbon monoxide. In these cases, the oxidation reaction catalyzed by the oxidation catalyst element may be represented by the following chemical equation:

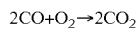

$$2CO + O_2 \rightarrow 2CO_2$$

In some instances, the method includes introducing a predetermined quantity of the one or more reagent gases into the carrier gas to produce a test gas contacting the oxidation catalyst element. For example, for an oxidation catalyst element the reagent gas may be carbon monoxide, and for a $\lambda$ value greater than 1, the concentration of the carbon monoxide in the test gas ranges from 1 ppmv to 25,000 ppmv, such as from 1 ppmv to 22,500 ppmv, or from 1 ppmv to 20,000 ppmv, or from 1 ppmv to 17,500 ppmv, or from 1 ppmv to 15,000 ppmv, or from 1 ppmv to 12,500 ppmv, or from 1 ppmv to 10,000 ppmv, or from 5 ppmv to 10,000 ppmv, or from 10 ppmv to 10,000 ppmv, or from 25 ppmv to 10,000 ppmv, or from 50 ppmv to 10,000 ppmv, or from 75 ppmv to 10,000 ppmv, or from 100 ppmv to 10,000 ppmv, or from 100 ppmv to 9000 ppmv, or from 100 ppmv to 8000 ppmv, or from 100 ppmv to 7000 ppmv, or from 100 ppmv to 6000 ppmv, or from 100 ppmv to 5000 ppmv, or from 100 ppmv to 4000 ppmv, or from 100 ppmv to 3000 ppmv, or from 100 ppmv to 2000 ppmv, or from 100 ppmv to 1000 ppmv, or from 200 ppmv to 1000 ppmv, or from 300 ppmv to 1000 ppmv, or from 400 ppmv to 1000 ppmv, or from 500 ppmv to 1000 ppmv, or from 600 ppmv to 1000 ppmv. In some instances, for an oxidation catalyst element at a $\lambda$ value greater than 1, the concentration of the reagent gas (carbon monoxide) in the test gas ranges from 10 ppmv to 10,000 ppmv. In some instances, for an oxidation catalyst element at a $\lambda$ value greater than 1, the concentration of the reagent gas (carbon monoxide) in the test gas ranges from 600 ppmv to 1000 ppmv.

In certain embodiments, for an oxidation catalyst element the reagent gas may include one or more hydrocarbons. For example, for an oxidation catalyst element at a $\lambda$ value greater than 1, the concentration of the one or more hydrocarbons in the test gas may range from 1 ppmv to 25,000 ppmv, such as from 1 ppmv to 22,500 ppmv, or from 1 ppmv to 20,000 ppmv, or from 1 ppmv to 17,500 ppmv, or from 1 ppmv to 15,000 ppmv, or from 1 ppmv to 12,500 ppmv, or from 1 ppmv to 10,000 ppmv, or from 5 ppmv to 10,000 ppmv, or from 10 ppmv to 10,000 ppmv, or from 25 ppmv to 10,000 ppmv, or from 50 ppmv to 10,000 ppmv, or from 75 ppmv to 10,000 ppmv, or from 100 ppmv to 10,000 ppmv, or from 100 ppmv to 9000 ppmv, or from 100 ppmv to 8000 ppmv, or from 100 ppmv to 7000 ppmv, or from 100 ppmv to 6000 ppmv, or from 100 ppmv to 5000 ppmv, or from 100 ppmv to 4000 ppmv, or from 100 ppmv to 3000 ppmv, or from 100 ppmv to 2000 ppmv, or from 100 ppmv to 1000 ppmv, or from 200 ppmv to 1000 ppmv, or from 300 ppmv to 1000 ppmv, or from 400 ppmv to 1000 ppmv, or from 500 ppmv to 1000 ppmv, or from 600 ppmv to 1000 ppmv. In some instances, for an oxidation catalyst element at a $\lambda$ value greater than 1, the concentration of the one or more hydrocarbons in the test gas ranges from 10 ppmv to 10,000 ppmv. In some instances, for an oxidation catalyst element at a $\lambda$ value greater than 1, the concentration of the one or more hydrocarbons in the test gas ranges from 600 ppmv to 1000 ppmv.

In some cases, for an oxidation catalyst element where the $\lambda$ value is greater than 1, the carrier gas includes oxygen. For example, for an oxidation catalyst element where the $\lambda$ value is greater than 1, the carrier gas can be air.

In some instances, the method is configured for testing the performance of a reduction catalyst element, such as a non-selective catalytic reduction (NSCR) emissions catalyst element. For the NSCR emissions catalyst element, the test gas may include one or more reductant gases and one or more oxidant gases. For example, the reagent gas can include two or more reagent gases, such as a reductant gas and an oxidant gas. The one or more reductant gases may be oxidized in an oxidation reaction catalyzed by the NSCR emissions catalyst element. The one or more oxidant gases may be reduced in a reduction reaction catalyzed by the NSCR emissions catalyst element. Examples of suitable reductant gases include, but are not limited to, carbon monoxide, gaseous aliphatic hydrocarbons (e.g., methane, ethane, propane, butane, etc.), gaseous olefinic hydrocarbons (e.g., ethene, propene, and butene, etc.), hydrogen, or mixtures thereof. Examples of suitable oxidant gases include, but are not limited to, nitric oxide, nitrogen dioxide, oxygen, or mixtures thereof. One or more reductant gases and one or more oxidant gases may be used in the methods and systems described herein to test the performance of a catalyst element.

In certain embodiments of the methods for testing the performance of an NSCR emissions catalyst element, the test gas flowing into the emissions catalyst element has a lambda ($\lambda$) value of 1 or less including oxygen present in the test gas. For instance, for the NSCR emissions catalyst element, the reagent gas may include a reductant gas and an oxidant gas, and the test gas flowing into the emissions catalyst element can has a λ value of 1 or less including oxygen present in the test gas. For example, for an NSCR emissions catalyst element, the lambda value (λ value) can be 1, or 1 or less, or less than 1, such as 0.9 or less, or 0.8 or less, or 0.7 or less, or 0.6 or less, or 0.5 or less.

In some instances, the NSCR emissions catalyst element catalyzes several reactions, such as, but not limited to: steam reforming reactions, where hydrocarbons and water vapor are consumed to produce carbon monoxide and hydrogen; water-gas shift reactions, where carbon monoxide and water vapor are consumed to produce hydrogen and carbon dioxide; and reduction reactions, where carbon monoxide, hydrogen and hydrocarbons are consumed to convert nitrogen oxides (such as, but not limited to, nitric oxide) into nitrogen.

In certain embodiments, the method is configured to test the performance of an NSCR emissions catalyst element by measuring the catalyst's effectiveness at catalyzing a reaction involving a reductant gas and an oxidant gas, such as a reaction involving carbon monoxide and nitric oxide. As such, in these cases, the test gas for an NSCR emissions catalyst element may include a reductant gas, such as carbon monoxide, and an oxidant gas, such as nitric oxide. In these cases, the reaction catalyzed by the NSCR emissions catalyst element may be represented by the following chemical equation:

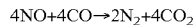
$$4NO + 4CO \rightarrow 2N_2 + 4CO_2$$

Examples of other reactions catalyzed by the NSCR emissions catalyst element include the reaction of nitric oxide with hydrogen to produce nitrogen and water, which may be represented by the following chemical equation:

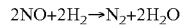
$$2NO + 2H_2 \rightarrow N_2 + 2H_2O$$

Examples of other reactions catalyzed by the NSCR emissions catalyst element include the reaction of nitric oxide with hydrocarbons (HC) to produce nitrogen, carbon dioxide and water, which may be represented by the following general chemical equation:

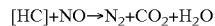
$$[HC] + NO \rightarrow N_2 + CO_2 + H_2O$$

For example, methane can react with nitric oxide to produce nitrogen, carbon dioxide and water, according to the following chemical equation:

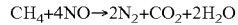
$$CH_4 + 4NO \rightarrow 2N_2 + CO_2 + 2H_2O$$

In some instances, the method includes introducing a predetermined quantity of the one or more reagent gases into the carrier gas to produce a test gas contacting the catalyst element. As described above, the test gas may include one or more reductant gases and one or more oxidant gases. For example, for an NSCR emissions catalyst element the reductant gas may be carbon monoxide, and for a λ value of 1 or less including oxygen present in the test gas, the concentration of the reductant gas (carbon monoxide) in the test gas ranges from 1 ppmv to 25,000 ppmv, such as from 1 ppmv to 22,500 ppmv, or from 1 ppmv to 20,000 ppmv, or from 1 ppmv to 17,500 ppmv, or from 1 ppmv to 15,000 ppmv, or from 1 ppmv to 12,500 ppmv, or from 1 ppmv to 10,000 ppmv, or from 5 ppmv to 10,000 ppmv, or from 10 ppmv to 10,000 ppmv, or from 25 ppmv to 10,000 ppmv, or from 50 ppmv to 10,000 ppmv, or from 75 ppmv to 10,000 ppmv, or from 100 ppmv to 10,000 ppmv, or from 100 ppmv to 9000 ppmv, or from 100 ppmv to 8000 ppmv, or from 100 ppmv to 7000 ppmv, or from 100 ppmv to 6000 ppmv, or from 100 ppmv to 5000 ppmv, or from 100 ppmv to 4000 ppmv, or from 100 ppmv to 3000 ppmv, or from 100 ppmv to 2000 ppmv, or from 100 ppmv to 1000 ppmv, or from 200 ppmv to 1000 ppmv, or from 300 ppmv to 1000 ppmv, or from 400 ppmv to 1000 ppmv, or from 500 ppmv to 1000 ppmv, or from 600 ppmv to 1000 ppmv, or from 700 ppmv to 1000 ppmv, or from 800 ppmv to 1000 ppmv. In some instances, for an NSCR emissions catalyst element at a λ value of 1 or less including oxygen present in the test gas, the concentration of the reductant gas (carbon monoxide) in the test gas ranges from 10 ppmv to 10,000 ppmv. In some instances, for an NSCR emissions catalyst element at a λ value of 1 or less including oxygen present in the test gas, the concentration of the reductant gas (carbon monoxide) in the test gas ranges from 800 ppmv to 1000 ppmv.

In some instances, for an NSCR emissions catalyst element the oxidant gas may be nitric oxide, and for a λ value of 1 or less including oxygen present in the test gas, the concentration of the oxidant gas (nitric oxide) in the test gas ranges from 1 ppmv to 50,000 ppmv, such as from 1 ppmv to 45,000 ppmv, or from 1 ppmv to 40,000 ppmv, or from 1 ppmv to 35,000 ppmv, or from 1 ppmv to 30,000 ppmv, or from 1 ppmv to 25,000 ppmv, or from 1 ppmv to 22,500 ppmv, or from 1 ppmv to 20,000 ppmv, of from 5 ppmv to 20,000 ppmv, or from 10 ppmv to 20,000 ppmv, or from 15 ppmv to 20,000 ppmv, or from 20 ppmv to 20,000 ppmv, or from 20 ppmv to 17,500 ppmv, or from 20 ppmv to 15,000 ppmv, or from 20 ppmv to 12,500 ppmv, or from 20 ppmv to 10,000 ppmv, or from 25 ppmv to 10,000 ppmv, or from 50 ppmv to 10,000 ppmv, or from 75 ppmv to 10,000 ppmv, or from 100 ppmv to 10,000 ppmv, or from 100 ppmv to 9000 ppmv, or from 100 ppmv to 8000 ppmv, or from 100 ppmv to 7000 ppmv, or from 100 ppmv to 6000 ppmv, or from 100 ppmv to 5000 ppmv, or from 100 ppmv to 4000 ppmv, or from 100 ppmv to 3000 ppmv, or from 100 ppmv to 2000 ppmv, or from 100 ppmv to 1000 ppmv, or from 200 ppmv to 1000 ppmv, or from 300 ppmv to 1000 ppmv, or from 300 ppmv to 900 ppmv, or from 300 ppmv to 800 ppmv, or from 300 ppmv to 700 ppmv, or from 400 ppmv to 7000 ppmv, or from 400 ppmv to 600 ppmv. In some instances, for an NSCR emissions catalyst element at a λ value of 1 or less including oxygen present in the test gas, the concentration of the oxidant gas (nitric oxide) in the test gas ranges from 20 ppmv to 20,000 ppmv. In some instances, for an NSCR emissions catalyst element at a λ value of 1 or less including oxygen present in the test gas, the concentration of the oxidant gas (nitric oxide) in the test gas ranges from 400 ppmv to 600 ppmv.

In some cases, for an NSCR emissions catalyst element where the λ value is 1 or less, the carrier gas is nitrogen. In some cases, for an NSCR emissions catalyst element where the λ value is 1 or less, the test gas is substantially free of oxygen. In certain instances, for an NSCR emissions catalyst element where the λ value is 1 or less, the test gas has 10,000 ppmv oxygen or less, such as 9,000 ppmv oxygen or less, or 8,000 ppmv oxygen or less, or 7,000 ppmv oxygen or less, or 6,000 ppmv oxygen or less, or 5,000 ppmv oxygen or less, or 4000 ppmv oxygen or less, or 3,000 ppmv oxygen or less, or 2,000 ppmv oxygen or less, or 1,000 ppmv oxygen or less, or 900 ppmv oxygen or less, or 800 ppmv oxygen or less, or 700 ppmv oxygen or less, or 600 ppmv oxygen or less, or 500 ppmv oxygen or less, or 400 ppmv oxygen or less, or 300 ppmv oxygen or less, or 200 ppmv oxygen or less, or 100 ppmv oxygen or less. For example, for an NSCR emissions catalyst element where the λ value is 1 or less, the test gas can include nitrogen with 600 ppmv oxygen or less.

In some instances, for an NSCR emissions catalyst element where the λ value is 1 or less, the test gas includes water vapor (i.e., water vapor is a reagent gas that is provided at a predetermined concentration in the test gas). For example, the test gas can include water vapor in an amount ranging from 0.5% to 10% by volume, such as 1% to 10%, or 2% to 9%, or 2% to 8% or 2% to 7%, or 2% to 6%, or 2% to 5%, or 2% to 4%, or 2% to 3% by volume. In some instances, the test gas can include water vapor in an amount ranging from 2% to 4% by volume.

In certain embodiments, the method for testing performance of the catalyst element includes measuring an inlet concentration of one or more reagent gases in the test gas in the gas flow path of the gas inlet. Measurement of the inlet concentration of the one or more reagent gases in the test gas can provide a baseline value for the concentration of the reagent gas or gases in the flow of the test gas before the test gas is contacted with the catalyst element. For example, the inlet concentration of the one or more reductant gases and/or one or more oxidant gases can be measured. Measuring the inlet concentration of the one or more reductant gases and/or one or more oxidant gases may facilitate providing the one or more reductant gases and/or one or more oxidant gases within a desired concentration range, such as the concentration ranges described above. In some cases, the method includes adjusting (i.e., increasing or decreasing) the concentration of the one or more reductant gases and/or one or more oxidant gases such that the concentration of the one or more reductant gases and/or one or more oxidant gases are at a desired concentration or within a desired concentration range. For example, adjusting the concentration of the one or more reagent gases can be achieved by adjusting the flow rates of the one or more reagent gases. An increase in the flow rate of a reagent gas that is mixed with the carrier gas to provide the test gas can provide an increase in the resulting concentration of that reagent gas in the test gas, whereas a decrease in the flow rate of a reagent gas that is mixed with the carrier gas to provide the test gas can provide a decrease in the resulting concentration of that reagent gas in the test gas. In cases where more than one reagent gas is used, the concentration of each individual reagent gas can be controlled separately.

Similarly, the amount (e.g., flow rate) of carrier gas used in the methods and systems can be controlled and adjusted as described herein.

The method for testing performance of the emissions catalyst element also includes measuring the outlet concentration of one or more reagent gases in the test gas in the gas flow path of the gas outlet. Measurement of the outlet concentration of the one or more reagent gases in the test gas can provide a value for the concentration of the reagent gas or gases after the test gas has been contacted with the catalyst element. For example, the outlet concentration of the reagent gas, such as the one or more reductant gases and/or one or more oxidant gases can be measured.

In some instances, the method includes determining the performance of the catalyst element based on the measured inlet concentration of the one or more reagent gases and the measured outlet concentration of the one or more reagent gases in the test gas. For example, the measured inlet concentration of the one or more reagent gases (e.g., the one or more reductant gases and/or the one or more oxidant gases) can be compared to the measured outlet concentration of the corresponding one or more reagent gases (e.g., the one or more reductant gases and/or the one or more oxidant gases), respectively. In some cases, if the catalyst element is functioning to reduce the amount of reagent gas, the measured outlet concentration of one or more reagent gases (e.g., one or more reductant gases and/or one or more oxidant gases) will be less than the measured inlet concentration of the corresponding reagent gas.

In certain embodiments, the measured outlet concentration of the one or more reagent gases (e.g., the one or more reductant gases and/or the one or more oxidant gases) can be compared to a threshold value. If the measured outlet concentration of the reagent gas (e.g., the one or more reductant gases and/or the one or more oxidant gases) is above the threshold value, this may be an indication that the catalyst element has unacceptable performance. If the measured outlet concentration of the reagent gas (e.g., the one or more reductant gases and/or the one or more oxidant gases) is below the threshold value, this may be an indication that the catalyst element has acceptable performance. In some instances, determining the performance of the catalyst element includes analyzing the measured inlet and outlet concentrations qualitatively and/or quantitatively. Qualitative determination includes determinations in which a simple yes/no or acceptable/unacceptable result is provided to a user with respect to the performance of the catalyst element. Quantitative determination includes both semi-quantitative determinations in which a rough scale result, e.g., low, medium, high, is provided to a user regarding the performance of the catalyst element and fine scale results in which an exact measurement of the performance of the catalyst element is provided to a user. For example, the method may include a quantitative measurement of the reduction in the concentration of the reagent gas (e.g., the one or more reductant gases and/or the one or more oxidant gases) by the catalyst element, or a quantitative measurement of the conversion efficiency of the catalyst element.

In certain embodiments, the method includes determining the performance of the catalyst element in real-time. As used herein, the terms "real-time", "measuring in real-time" and "real-time measurement" are interchangeable and refer to measuring a parameter as it occurs or immediately thereafter. In some cases, the method provides for continuous real-time measurement of the performance of the catalyst element.

In other embodiments, the performance of the catalyst element may be determined "offline". As used herein, "offline" or "offline processing" refers to methods where data is stored and then analyzed at a later date. For example, the method may include storing the measured inlet and outlet concentrations of the test gas, and then subsequently analyzing the stored data to determine the performance of the catalyst element.

Systems

Aspects of the present disclosure include systems for testing performance of a catalyst element, such as but not limited to an emissions catalyst element. In some instances, the catalyst element is an emissions catalyst element, such as an oxidation emissions catalyst element or an NSCR emissions catalyst element.

The system includes a gas source (e.g., a source of a gas stream). The gas source may be configured to provide a flow of a gas through the system (e.g., through a gas flow path of the system). For instance, the gas source may be configured to provide a flow of air and/or a carrier gas and/or a test gas through the gas flow path of the system. In addition, the system may include one or more conduits configured to carry a flow of the gas stream through the system. The conduits of the system (along with the gas inlet and gas outlet described herein) may define the gas flow path of the system. The conduits may be of any convenient size and shape, as long as the conduits are of sufficient size and shape to carry the desired volume of gas at the desired flow rate to adequately perform testing of the catalyst element. For example, the conduits may have a circular cross sectional area (e.g., the conduits may be configured in the shape of a cylinder). Other conduit shapes are also possible, such as, but not limited to, conduits with a cross sectional area of an ellipse, a square, a rectangle, or other polygonal shape.

The system also includes a gas inlet. The gas inlet is configured to seal against an upstream surface of a catalyst element. The gas inlet is configured to provide a substantially gas-tight seal against the upstream surface of the catalyst element. As described above, in some instances, a gasket may be provided between the gas inlet and the upstream surface of the catalyst element, which may facilitate forming a gas-tight seal between the gas inlet and the upstream surface of the catalyst element. The gas inlet may be of any convenient size and shape, as long as the gas inlet is of sufficient size and shape to carry the desired volume of gas at the desired flow rate to adequately perform testing of the catalyst element. For example, the gas inlet may have a circular cross sectional area. Other gas inlet shapes are also possible, such as, but not limited to, a gas inlet with a cross sectional area of an ellipse, a square, a rectangle, or other polygonal shape.

The system also includes a gas outlet. The gas outlet is configured to seal against a downstream surface of the catalyst element. The gas outlet is configured to provide a substantially gas-tight seal against the downstream surface of the catalyst element. As described above, in some instances, a gasket may be provided between the gas outlet and the downstream surface of the catalyst element, which may facilitate forming a substantially gas-tight seal between the gas outlet and the downstream surface of the catalyst element. The gas outlet may be of any convenient size and shape, as long as the gas outlet is of sufficient size and shape to carry the desired volume of gas at the desired flow rate to adequately perform testing of the catalyst element. For example, the gas outlet may have a circular cross sectional area. Other gas outlet shapes are also possible, such as, but not limited to, a gas outlet with a cross sectional area of an ellipse, a square, a rectangle, or other polygonal shape.

In embodiments of the presently disclosed system, the cross sectional area of the gas inlet is less than the cross sectional area of the gas outlet. For example, for gas inlets and gas outlets having circular cross sectional areas, the diameter of the gas inlet is less than the diameter of the gas outlet. Stated another way, the inner diameter of the conduit forming the gas inlet may be less than the inner diameter of the conduit forming the gas outlet. A gas inlet with a smaller cross sectional area than the gas outlet may facilitate mounting of the catalyst element between the gas inlet and the gas outlet. For example, it may not be necessary to precisely align the peripheral edges of the gas inlet and gas outlet with each other if the gas inlet has a smaller cross sectional area than the gas outlet. In some instances, a gas inlet with a smaller cross sectional area than the gas outlet may facilitate sealing between the gas inlet, catalyst element, and gas outlet, such that there is a minimization in gas leakage from the system. In some instances, where the gas inlet has a smaller cross sectional area than the gas outlet, the gas inlet and gas outlet may be concentrically aligned with each other. In other instances, the gas inlet and gas outlet do not need to be concentrically aligned with each other, while maintaining the inlet cross section within the perimeter of the outlet cross section, while still achieving gas-tight seals between the gas inlet, the gas outlet, and the respective surfaces of the catalyst element (and/or gaskets provided between the gas inlet or gas outlet and the catalyst element).

As described above, the performance of the catalyst element can be determined at two or more distinct regions of the catalyst element. Thus, a dimension of the gas inlet (e.g., the diameter of the gas inlet) is less than or equal to a dimension of the catalyst element (e.g., a dimension of the upstream surface of the catalyst element) such that the gas inlet seals against a portion of the upstream surface of the catalyst element. Similarly, a dimension of the gas outlet (e.g., the diameter of the gas outlet) is less than or equal to a dimension of the catalyst element (e.g., a dimension of the downstream surface of the catalyst element) such that the gas outlet seals against a portion of the downstream surface of the catalyst element. Although the dimensions (diameters) of both the gas inlet and gas outlet may be smaller than the dimensions of the catalyst element, the gas inlet may still have a smaller cross sectional area than the gas outlet as described above.

In certain embodiments, the system includes a detector. Examples of detectors include portable gas analyzers, such as the Testo model 350, FTIR gas analyzer, and the like. The detector may be configured to measure the concentration of a reagent gas (e.g., the reductant gas and/or the oxidant gas). In some cases, the detector is configured to measure the concentration of one or more reagent gases in the test gas upstream from the gas inlet (e.g., upstream from the catalyst element). In some cases, the detector is configured to measure the concentration of one or more reagent gases in the test gas downstream from the gas outlet (e.g., downstream from the catalyst element). In some embodiments, two detectors are included in the system, such as an upstream detector and a downstream detector. In other embodiments, the same detector can be used to first measure the concentration of the one or more reagent gases in the test gas upstream from the catalyst element, and then subsequently measure the concentration of the one or more reagent gases in the test gas downstream from the catalyst element.

Embodiments of the system also include a processor. The processor may be operatively connected to the detector, such that data can be exchanged between the processor and the detector. For example, data relating to the measured concentration of the reagent gas upstream from the catalyst element and the measured concentration of the reagent gas downstream from the catalyst element may be transmitted between the processor and detector (e.g., from the detector to the processor or vice versa). The processor may be configured to determine the performance of the catalyst element based on the measured inlet concentration and the measured outlet concentration of the reagent gas, as described herein.

In certain embodiments, the system is configured to accommodate the flow of a gas through the gas flow path of the system at a flow rate ranging from 0.1 SCFM to 50 SCFM, such as from 0.5 SCFM to 45 SCFM, or from 0.5 SCFM to 40 SCFM, or from 0.5 SCFM to 35 SCFM, or from 0.5 SCFM to 30 SCFM, or from 0.5 SCFM to 25 SCFM, or from 0.5 SCFM to 20 SCFM, or from 0.5 SCFM to 15 SCFM, or from 0.5 SCFM to 10 SCFM. For example, system may be configured to accommodate a flow of a gas through the gas flow path at a flow rate ranging from 0.5 SCFM to 20 SCFM.

In certain embodiments, the system includes a gas controller. Examples of gas controllers include, but are not limited to, a rotameter with a flow control valve, a mass flow controller, a critical orifice, and the like. The gas controller may be configured to control the flow rate of a gas stream (e.g., air, carrier gas, reagent gas, test gas, combinations thereof, etc.) through the gas flow path of the system. Where desired, the controller is configured to adjust the flow rate of the gas stream depending on the desired parameters for testing the performance of the catalyst element. For example, the controller can be configured to reduce the flow rate of the gas stream. The controller can also be configured to increase the flow rate of the gas stream.

In some cases, the system includes one or more sources of pressurized gas. Examples of pressurized gas sources include blowers, compressors, and pressurized gas cylinders. These pressurized gas sources facilitate the movement of the gas stream through the system. In certain embodiments, the pressurized gas source facilitates the movement of air, a carrier gas, a reagent gas, a test gas, or combinations thereof, through the system. For example, the system may include one or more of a pressurized source of a carrier gas, and a pressurized source of a reagent gas. A pressurized gas source may be positioned upstream from the catalyst element. In these cases, the pressurized gas source may be configured to push the gas stream through the system. For instance, the pressurized gas source may be configured to push the gas stream downstream through the system. In certain embodiments, the systems include one or more exhausters. Similar to a pressurized gas source, the exhausters may facilitate the movement of a gas stream through the system. In certain cases, the exhausters facilitate movement of air, a carrier gas, a reagent gas, a test gas, or combinations thereof, through the system. An exhauster may be positioned downstream from the catalyst element. In these cases, the exhauster may be configured to pull a gas stream through the system. For example, the exhauster may be configured to pull the gas stream downstream through the system. The pressurized gas source and/or the exhauster may be controlled by the gas controller of the system.

In certain embodiments, the gas controller is configured to control the composition of the gas stream flowing through the system. For example, the gas controller may be configured to control the amount and/or composition of the carrier gas flowing through the system. The amount and/or composition of the carrier gas may depend on the type of catalyst element being tested. For instance, as described herein, the carrier gas may be air for an oxidation catalyst element where the λ value is greater than 1. In other cases, as described herein, the carrier gas may be an inert gas (e.g., nitrogen) for an NSCR catalyst element where the λ value is 1 or less. In some of these instances, as described herein, the carrier gas and/or the test gas may also include water vapor. As such, the gas controller may be configured to control the amount and/or composition of the carrier gas such that the desired amount and/or composition of the carrier gas is flowed through the system.

In certain embodiments, the gas controller is configured to control the composition of the test gas flowing through the system. For instance, the gas controller may be configured to provide a predetermined concentration of one or more reagent gases to be mixed with the carrier gas to produce the test gas. In some cases, the gas controller may be configured to provide a predetermined quantity of one or more reagent gases to the carrier gas flowing through the system. The composition of the test gas may depend on the type of catalyst element being tested. For example, as described herein, the test gas may include one or more reductant gases for testing an oxidation catalyst element, or may include one or more reductant gases and one or more oxidant gases for testing an NSCR catalyst element. In some cases, the gas controller is configured to control the flow rate of the reagent gas. For example, the gas controller can control the flow rate of the reagent gas by increasing or decreasing the flow rate of the reagent gas. An increase in the flow rate of the reagent gas that is mixed with the carrier gas to provide the test gas can provide an increase in the desired concentration of the reagent gas in the test gas, whereas a decrease in the flow rate of the reagent gas that is mixed with the carrier gas to provide the test gas can provide a decrease in the desired concentration of the reagent gas in the test gas. In cases where more than one reagent gas is used, individual gas controllers may be provided to control the flow rate of each reagent gas separately. Similarly, a separate carrier gas controller may be used to individually control the flow rate of the carrier gas.

In certain embodiments, the system includes one or more flow regulators. The flow regulators may be configured to regulate the flow of a gas through the system. For example, a flow regulator may be configured to regulate the flow of one or more of air, a carrier gas, a reagent gas, a test gas, or combinations thereof, through the system. In some cases, individual flow regulators may be provided to regulate the flow of the various gases (e.g., the carrier gas and the reagent gas(es)) through the system. The flow regulators may include, but are not limited to, dampers, valves, solenoids, and the like. The one or more flow regulators in the system may be controlled by the gas controller.

The components of the system may be exposed to harsh conditions, such as high temperature, corrosive gases, corrosive liquids, and the like. As such, the components of the system may be composed of a material that is able to function under harsh conditions without significant structural degradation, decomposition, or corrosion. In certain instances, the components of the system are made of a substantially inert material, such as stainless steel, and the like.

In certain instances, the system includes a heater. The heater may be configured to heat a gas flowing through the system, such as air, a carrier gas, a reagent gas, a test gas, combinations thereof, etc. In some instances, the heater is configured to heat air flowing through the system. In some instances, the heater is configured to heat a carrier gas flowing through the system. In some instances, the heater is configured to heat a test gas (e.g., a mixture of the carrier gas and reagent gas(es)) flowing through the system. The heater may be configured to heat the gas to a desired temperature, as described herein. In some cases, the heater is controlled by the gas controller of the system.

In some cases, the system also includes a display for outputting data and/or results to a user in a human-readable format. In certain instances, the system also includes a communication link for communicating with other devices, such as, but not limited to, a wired communication link (e.g., a USB, serial, Ethernet, or parallel interface, and the like), or a wireless communication link (e.g., Bluetooth, WiFi, cellular, infrared, RF, and the like).

In certain embodiments, the system includes a catalyst element positioned in the gas flow path of the system. In certain instances, the gas stream flows through the system including the catalyst element, where the gas stream contacts the catalyst of the catalyst element.

Computer Related Embodiments

A variety of computer-related embodiments are also provided. Specifically, the data analysis methods described herein may be performed using a computer, e.g., a processor. Accordingly, provided is a computer-based system for analyzing data produced using the above methods and systems in order to provide qualitative and/or quantitative analysis of a target area of interest in a subject.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include CD-ROM, DVD-ROM, BD-ROM, a hard disk drive, a ROM or integrated circuit, a magneto-optical disk, a solid-state memory device, a computer readable flash memory, and the like, whether or not such devices are internal or external to the computer. A file containing information may be "stored" on computer readable medium, where "storing" means recording information such that it is accessible and retrievable at a later date by a computer (e.g., for offline processing). Examples of media include, but are not limited to, non-transitory media, e.g., physical media in which the programming is associated with, such as recorded onto, a physical structure. Non-transitory media for storing computer programming does not include electronic signals in transit via a wireless protocol.

In certain embodiments, computer programming may include instructions for directing a computer to perform one or more steps of the methods disclosed herein. For example, the computer programming may include instructions for directing a computer to detect and/or analyze signals acquired by the systems (e.g., detectors) disclosed herein. In certain embodiments, the computer programming includes instructions for directing a computer to analyze the measured concentration data qualitatively and/or quantitatively. Qualitative determination includes determinations in which a simple yes/no or acceptable/unacceptable or pass/fail result is provided to a user with respect to the performance of an emissions catalyst element. Quantitative determination includes both semi-quantitative determinations in which a rough scale result, e.g., low, medium, high, is provided to a user regarding the performance of an emissions catalyst element and fine scale results in which an exact measurement of the performance of an emissions catalyst element is provided to a user.

With respect to computer readable media, "permanent memory" refers to memory that is not erased by termination of the electrical supply to a computer or processor. Computer hard-drive, CD-ROM, DVD-ROM, BD-ROM, and solid state memory are all examples of permanent memory. Random Access Memory (RAM) is an example of non-permanent memory. A file in permanent memory may be editable and re-writable. Similarly, a file in non-permanent memory may be editable and re-writable.

Utility

The systems and methods of the present disclosure find use in a variety of different applications where it is desirable to test the performance of a catalyst element, such as an emissions catalyst element, e.g., an oxidation emissions catalyst element or an NSCR emissions catalyst element. Any oxidation catalyst element or reduction catalyst element can be tested using the subject systems and methods. For example, the subject testing methods can be applied to either an oxidation catalyst element or a reduction catalyst element using the same system. The composition of the carrier gas, reagent gas, test gas, etc. can be adjusted accordingly to provide the desired carrier gas, reagent gas, test gas, etc. appropriate for testing either an oxidation catalyst element or a reduction catalyst element. As such, the systems and methods of the present disclosure find use in testing the performance of catalyst elements at various lambda ($\lambda$) values, such as at $\lambda$ values greater than 1, or at $\lambda$ values of 1 or less (including oxygen present in the test gas). In some instances, systems of the present disclosure may be referred to as Multi-Lambda Catalyst Test System™ or MLCTS™.

The systems and methods of the present disclosure can be used to test any gas phase reaction catalyst element. For example, any type of catalyst element used for catalysis of gas phase reactions (e.g., oxidation or reduction reactions, or any other type of gas phase reactions) can be tested using the methods and systems of the present disclosure. Examples include, but are not limited to, oxidation or reduction catalyst elements, such as catalyst elements used in pharmaceutical research, pharmaceutical manufacturing, academic research, and the like.

In addition, the subject systems and methods find use in rapid testing protocols. For example, since the systems and methods can be adjusted for any desired oxidation catalyst element or reduction catalyst element, the subject systems and methods find use in field testing protocols. In some instances, the subject systems are portable systems that can be easily transported from one location to another. In some instances, the subject systems and methods find use in testing the performance of various sizes of catalyst elements, so long as the catalyst elements are of a size compatible with the system (e.g., large enough to form a substantially gas-tight seal with the gas inlet and gas outlet and small enough to be compatible with the dimensions of the system). As described herein, the systems and methods may be configured to include an adjustable gas inlet and an adjustable gas outlet to facilitate mounting various sizes catalyst elements in the system. After positioning the catalyst element in the system, the positions of the gas inlet and/or gas outlet can be adjusted such that sufficient gas-tight sealing contact is achieved between the gas inlet and the upstream surface of the catalyst element and between the gas outlet and the downstream surface of the catalyst element. In addition, the subject systems and methods find use in testing the performance of various shapes of catalyst elements (e.g. round, rectangular, polygonal, or other monolithic shapes with substantially flat and parallel faces that can form substantially gas-tight seals with the gas inlet and gas outlet of the system). As described herein, the systems and methods may be configured to include a gas inlet and a gas outlet that have dimensions (diameters) smaller than the dimensions of the catalyst element to be tested. This facilitates positioning the gas inlet and gas outlet in contact with a portion of the catalyst element, such that the gas inlet and gas outlet do not need to seal against the entire periphery of variously shaped catalyst elements.

In certain embodiments, the subject systems and methods find use in testing protocols where there is a desire to minimize false positive results. For example, a false positive result (e.g., a false result overstating the performance of the emissions catalyst element) may lead to excessive emissions of air pollutants into the atmosphere. In other cases, the subject systems and methods find use in testing protocols where there is a desire to minimize false negative results. For example, a false negative result (e.g., a false result understating the performance of the emissions catalyst element) may lead to loss of time and money spent unnecessarily replacing an acceptable catalyst element.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by volume, molecular weight is weight average molecular weight, temperature is in degrees Celsius, and pressure is at or near atmospheric.

EXAMPLES

Example 1

An example of a system according to the present disclosure is shown in FIG. 1. On this system, the gases are supplied through various connections; the air through gas line (1), Nitrogen gas through gas line (2), Oxidant gas (e.g., NO) through gas line (3), and reductant gas through gas line (4). For this example a portable gas analyzer (5) is utilized. The detail of the location of gas outlet (6) is shown in FIG. 4.

Figure 2A:
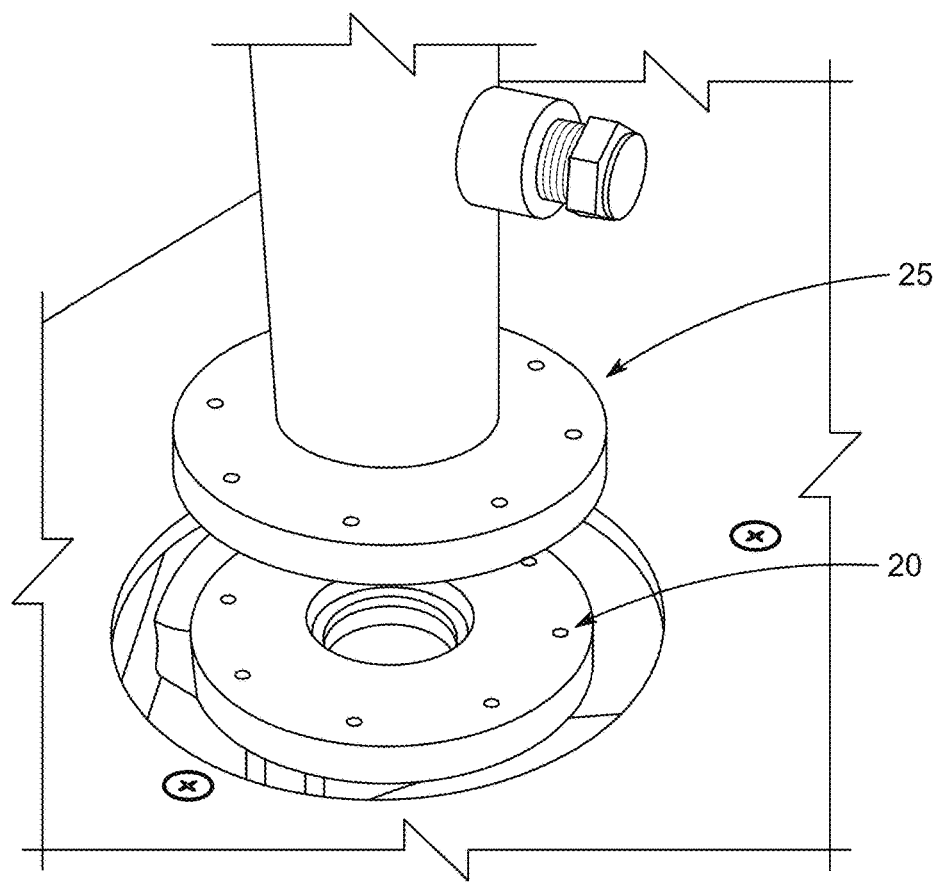
FIG. 2A and FIG. 2B show images of the gas inlet and gas outlet of a system for testing the performance of a catalyst element, according to embodiments of the present disclosure.
Figure 2B:
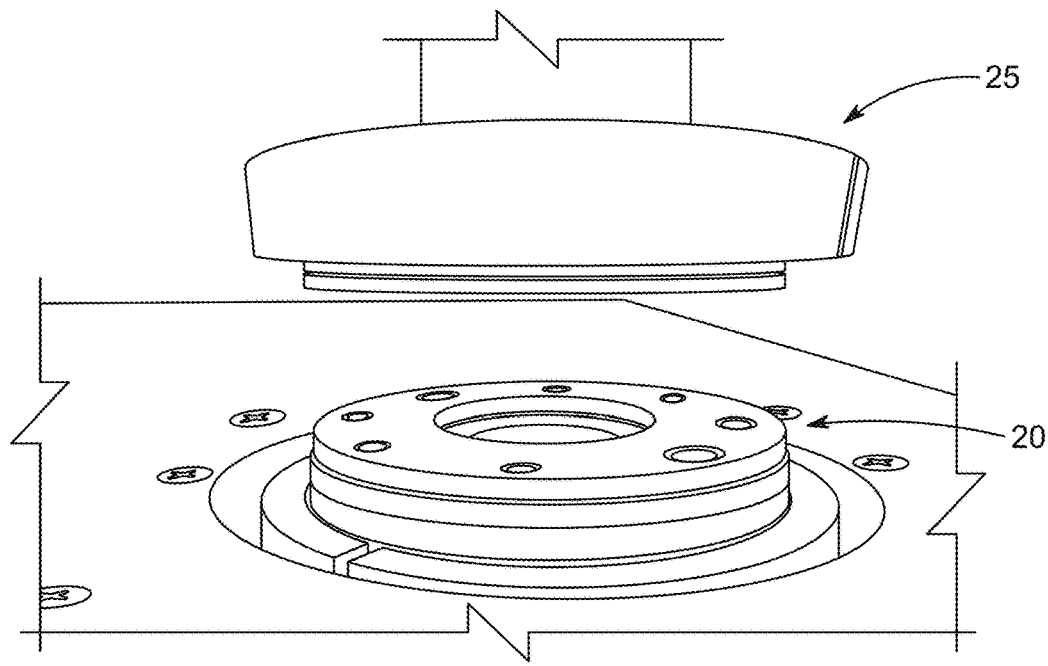

FIG. 2A and FIG. 2B show images of the gas inlet (20) and gas outlet (25) of a system for testing the performance of a catalyst element. The gas inlet (20) has a smaller cross sectional area than the cross sectional area of the gas outlet (25). Stated another way, the inner diameter of the conduit forming the gas inlet is less than the inner diameter of the conduit forming the gas outlet.

Figure 3:
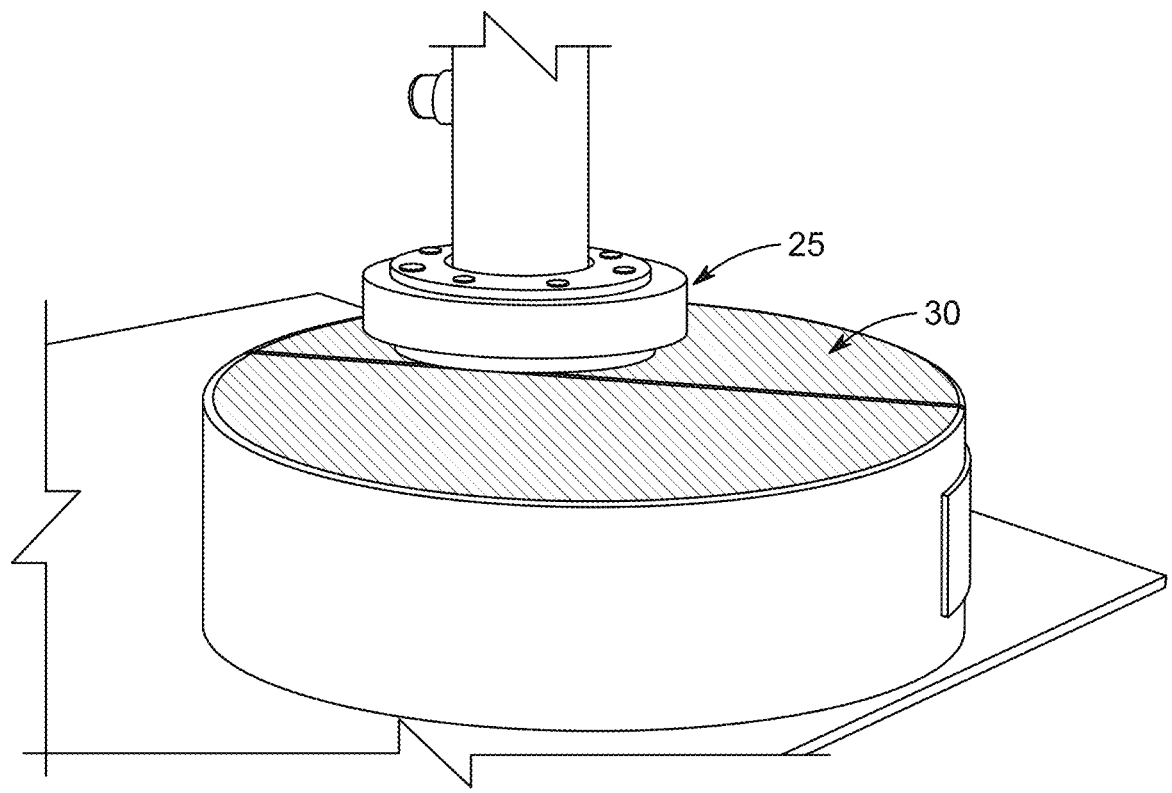
FIG. 3 shows an image of a catalyst element mounted in a system for testing the performance of a catalyst element, according to embodiments of the present disclosure.

FIG. 3 shows an image of a catalyst element (30) mounted in a system for testing the performance of the catalyst element. A portion of the catalyst element is mounted between the gas inlet (not shown) and the gas outlet (25).

Figure 4:
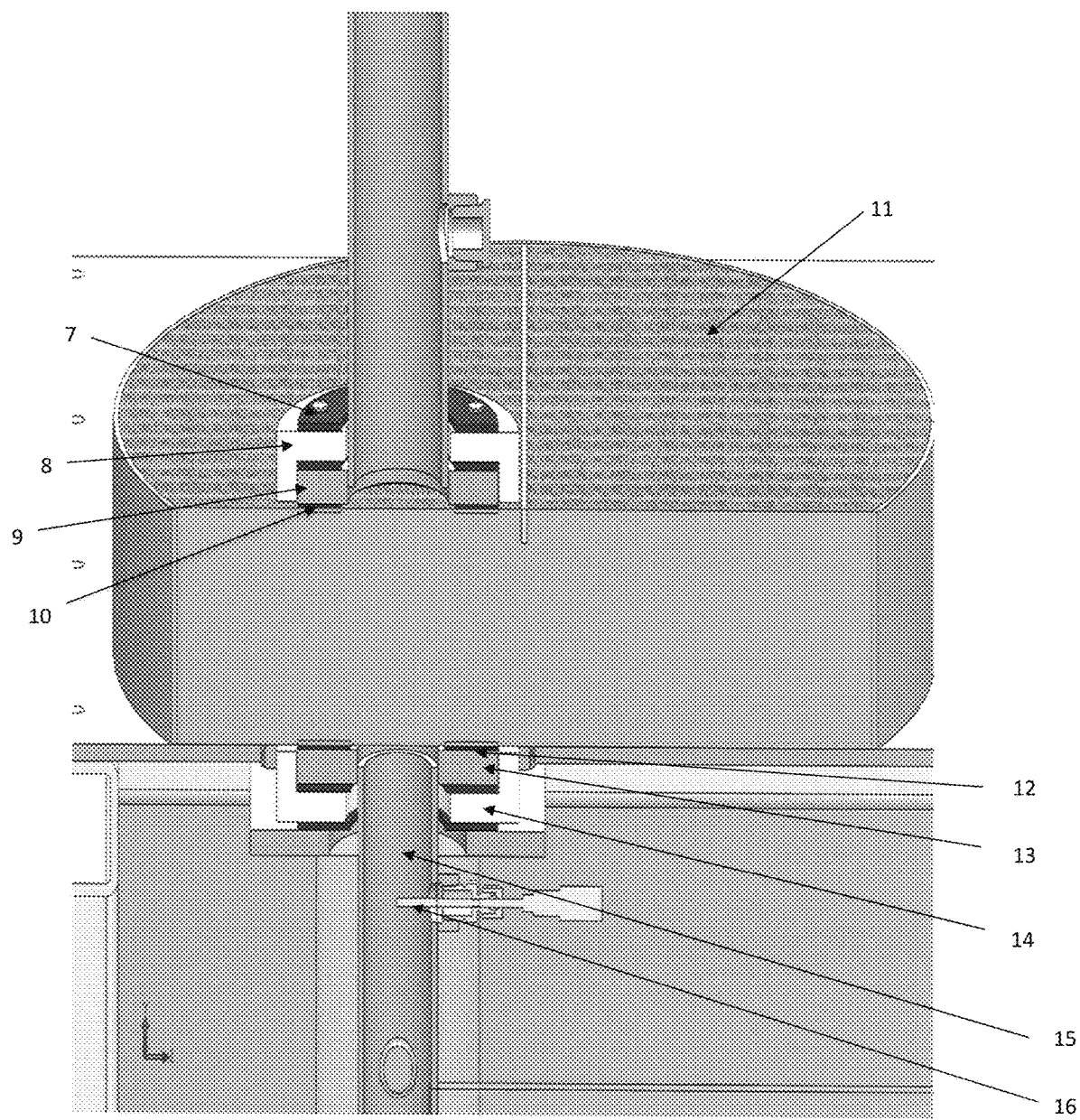
FIG. 4 shows a cross sectional detail of the catalyst element mounted in the system, according to embodiments of the present disclosure.

FIG. 4 shows a cross sectional detail of the gas path from the gas inlet (20), the catalyst element (30), and the gas outlet (25) as shown in FIGS. 2 and 3. As shown in FIG. 4, the system includes an outlet head that includes a graphite plate (7), a ceramic insulating guard (8), a stainless steel flange (9), and a graphite gasket (10). As shown in FIG. 4, the system also includes an inlet head that includes a graphite gasket (12), a stainless steel flange (13), a ceramic insulating guard (14), an inlet pipe (15), and an inlet (process) thermocouple (16). The catalyst element (11) to be tested is mounted between the gas inlet and the gas outlet as described herein.

Example 2

Comparative experiments were performed to test the performance of an NSCR emissions catalyst element.

A performance test of an NSCR emissions catalyst element was performed with a conventional test system and method using heated air as the carrier gas and propane as the reagent gas. The conventional test system and method indicated that the NSCR emissions catalyst element had an activity level of 5% of the maximum value. The results of the conventional test system and method indicated that the first NSCR emissions catalyst element had unacceptable performance and should be replaced.

Figure 5:
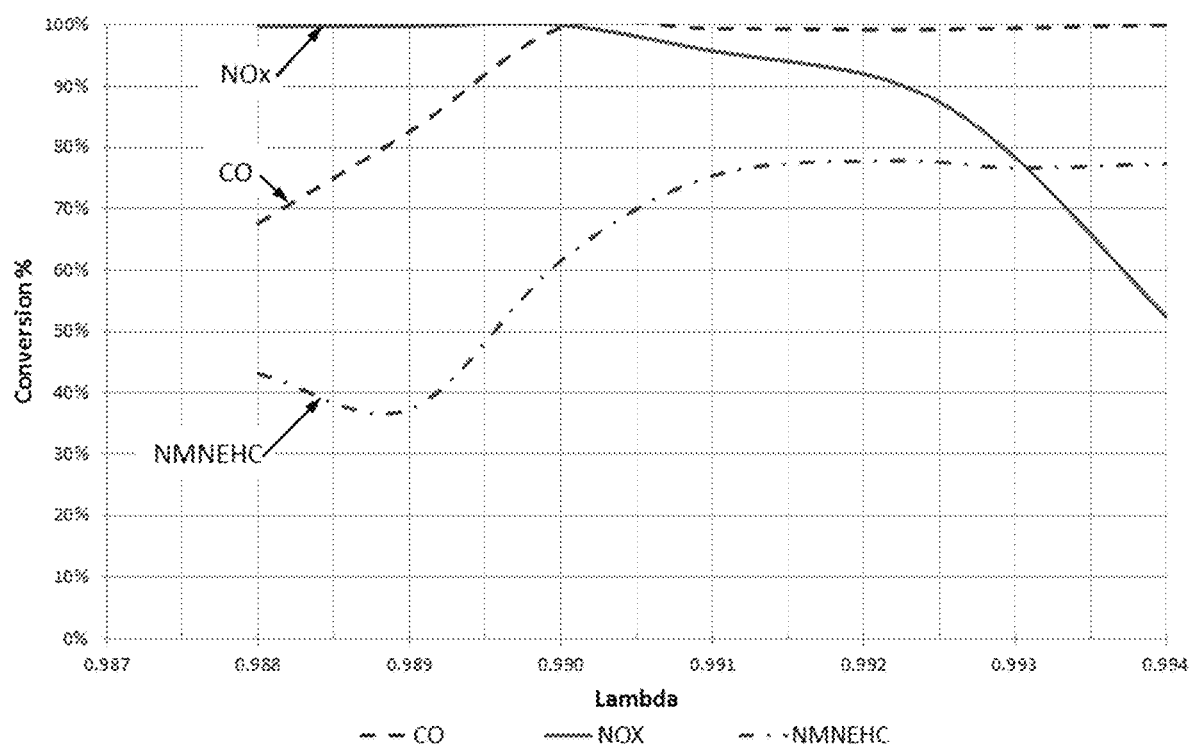
FIG. 5 shows a graph of conversion % vs. lambda for a performance test of an NSCR catalyst element using a test system and method according to embodiments of the present disclosure.

FIG. 5 shows a graph of conversion % vs. lambda for a performance test of the same NSCR emissions catalyst element using a test system and method according to embodiments of the present disclosure. Curves for NOx, CO and NMNEHC (non-methane, non-ethane hydrocarbons) are shown in the graph. As shown in FIG. 5, the results indicated >99% conversion of NOx and CO at the cross-over point.

The results of the comparative experiments indicated that a conventional test system and method produced a false negative result, whereas the test system and method according to embodiments of the present disclosure did not produce a false negative result.

Example 3

A series of tests were performed on numerous NSCR catalysts in various stages of their lifecycle. The testing conditions chosen were selected to show the greatest difference in small changes in catalyst health. The results of these tests are shown in Table 1 (see FIG. 6), and are discussed in detail herein. The MLCTS system was operated in NSCR mode (Nitrogen Carrier), with the test gas composition of approximately 1300 ppm NOx, 700 ppm CO, 2 g/min of steam, and Oxygen adjusted to give a test gas lambda of 0.992-0.994 (nominal 0.993). The test gas was introduced to the catalyst at a space velocity of 207,000 $hr^{-1}$ and an inlet temperature of 900° F. In these examples, the term "washing" is used. For the purposes of these examples the term "washing" refers to the utilization of a primary chemical cleaning process which is designed to remove deactivating contaminants from the catalyst.

Cat1 was a sample of new catalyst formulation which had undergone a degreening process and represented an initial installation performance level. This catalyst under these conditions showed excellent NOx reduction and moderate CO reduction. The NOx DRE is indicative of the general health of the catalyst overall, in this case a healthy catalyst. The CO DRE gives an insight into the health of the oxygen storage component (OSC) and other characteristics of the catalyst formulation, again a healthy catalyst was indicated.

Cat2 was a sample of a new catalyst of a standard formulation which had undergone a degreening process and represented the initial installation performance level. This catalyst under these conditions showed excellent NOx reduction and very good CO reduction. These results, as expected for a new catalyst, indicated a healthy catalyst.

Cat3 was a sample of catalyst of the same formulation as Cat2 which had undergone a degreening process and represented the initial installation performance level. This catalyst again yielded results indicative of a healthy catalyst.

Cat4 was a catalyst sample that had been operated in the field for an undetermined number of hours. The element was returned for cleaning and testing. The results indicated reasonably good NOx performance but actual production of CO across the catalyst. These results indicated that with respect to NOx reduction the catalyst was healthy, however, the production of CO indicated a potential issue with the OSC that required further evaluation determine the overall health of the catalyst.

Cat5 was a catalyst sample that had been operated in the field for an undetermined number of hours. It was returned for washing. The results indicated a moderate NOx performance and low CO performance which lead to a recommendation to replace the catalyst.

Cat6 was a catalyst sample that had been operated in the field for an undetermined number of hours. It was returned for washing. After washing the catalyst was exhibiting a large amount of exfoliation and was re-tested. The results showed poor NOx and CO performance indicating that the catalyst should be replaced.

Cat 7 was a catalyst sample that had been returned from the field for washing. After washing, like Cat 6, the catalyst exhibited an extreme amount of exfoliation. Testing results showed very poor NOx and CO performance and is a prime example of catalyst that must be replaced.

Example 4

A series of tests were performed on numerous oxidation catalysts in various stages of their lifecycle. The testing conditions chosen were selected to show the greatest difference in small changes in catalyst health. The results of these tests are contained in Table 2 (see FIG. 7), and are discussed in detail herein. The MLCTS system was operated in oxidation mode (Air Carrier), with the test gas composition of approximately 700 ppm CO. The test gas was introduced to the catalyst at a space velocity of 305,000 $hr^{-1}$ and an inlet temperature of 500° F.

Cat 8 was an oxidation catalyst that was produced for laboratory testing and had undergone a degreening procedure. The catalyst was tested under the above conditions. The CO DRE was taken as the baseline for a healthy catalyst.

Cat 9 was an oxidation catalyst that was operated in the field for a period of at least 3 operating years, hours of operation are unknown. The catalyst showed moderate CO performance and indicated that the catalyst should be evaluated either on a reactor under application conditions before placing back in service.

Cat 10 was an oxidation Catalyst that was operated in the field for approximately 9 months and was returned for non-performance. Washing and testing using the MLCTS system described above confirmed underperformance. Through elemental testing, the catalyst was found to have been poisoned and reclaimed.

Cat 11 was an oxidation catalyst that was operated in the field for an unknown period. After washing the catalyst was tested using the MLCTS system described above and showed excellent performance, however, because of mechanical damage was replaced.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for testing performance of an oxidation catalyst element or a non-selective catalytic reduction catalyst element, the method comprising:
   mounting a catalyst element in a gas flow path of a system comprising a gas inlet upstream from the catalyst element and a gas outlet downstream from the catalyst element;
   introducing a predetermined quantity of one or more reagent gases into a carrier gas to produce a test gas flowing through the gas flow path of the gas inlet;
   measuring an inlet concentration of the one or more reagent gases in the test gas in the flow path of the gas inlet;
   measuring an outlet concentration of the one or more reagent gases in the test gas in the flow path of the gas outlet; and
   determining the performance of the catalyst element by calculating the Destruction and Removal Efficiency (DRE) of the catalyst element for the one or more reagent gases based on the measured inlet concentration of the one or more reagent gases and the measured outlet concentration of the one or more reagent gases,
   wherein, for the oxidation catalyst element, the one or more reagent gases comprise one or more reductant gases, and the test gas flowing into the emissions catalyst element has a $\lambda$ value of greater than 1, and
   wherein, for the non-selective catalytic reduction catalyst element, the one or more reagent gases comprise one or more reductant gases and one or more oxidant gases, and the test gas flowing into the emissions catalyst element has a $\lambda$ value of 1 or less including oxygen present in the test gas.

2. The method of claim 1, wherein the reductant gas comprises carbon monoxide, gaseous aliphatic hydrocarbons, gaseous olefinic hydrocarbons, hydrogen, or mixtures thereof.

3. The method of claim 1, wherein the oxidant gas comprises nitric oxide, nitrogen dioxide, oxygen, or mixtures thereof.

4. The method of claim 1, wherein the carrier gas flowing through the gas flow path for a $\lambda$ value greater than 1 comprises air.

5. The method of claim 1, wherein the carrier gas flowing through the gas flow path for a $\lambda$ value of 1 or less comprises an inert gas.

6. The method of claim 1, wherein the test gas further comprises water vapor.

7. The method of claim 1, wherein the test gas flowing through the gas flow path for a $\lambda$ value of 1 or less contains oxygen.

8. The method of claim 1, wherein the test gas comprises carbon monoxide in a predetermined concentration ranging from 10 ppmv to 10,000 ppmv for a $\lambda$ value greater than 1.

9. The method of claim 1, wherein the test gas comprises one or more hydrocarbons in a predetermined concentration ranging from 10 ppmv to 10,000 ppmv for a $\lambda$ value greater than 1.

10. The method of claim 1, wherein the test gas comprises nitrogen oxides in a predetermined concentration ranging from 20 ppmv to 20,000 ppmv, and a reductant gas of a concentration to yield a $\lambda$ value of 1 or less.

11. The method of claim 1, wherein the method comprises heating the carrier gas in the gas flow path before introducing the reagent gas into the carrier gas.

12. The method of claim 1, wherein the method further comprises mixing the reagent gas with the carrier gas to produce the test gas.

13. The method of claim 12, wherein the test gas in the gas flow path at the gas inlet has a temperature ranging from 212° F. (100° C.) to 1100° F. (593° C.).

14. The method of claim 12, wherein the test gas flowing through the gas flow path has a flow rate ranging from 0.5 SCFM to 20 SCFM.

15. The method of claim 1, wherein the method comprises quantitatively determining the performance of the catalyst element in real time.

16. The method of claim 1, wherein the method comprises determining the performance of the catalyst element at two or more distinct regions of the catalyst element.

17. A system for testing performance of an oxidation catalyst element or a non-selective catalytic reduction catalyst element, the system comprising:
- a gas source that provides a flow of a carrier gas through the system;
- a gas inlet to a catalyst element that seals against an upstream surface of the catalyst element;
- a gas outlet from the catalyst element that seals against a downstream surface of the catalyst element;
- a detector that measures a concentration of one or more reagent gases in a test gas upstream from the gas inlet or measures a concentration of the one or more reagent gases in the test gas downstream from the gas outlet; and
- a processor that determines the performance of the catalyst element by calculating the Destruction and Removal Efficiency (DRE) of the catalyst element for the one or more reagent gases based on the measured inlet concentration of the one or more reagent gases and measured outlet concentration of the one or more reagent gases, wherein, for the oxidation catalyst element, the one or more reagent gases comprise one or more reductant gases, and the test gas flowing into the catalyst element has a $\lambda$ value of greater than 1, and wherein, for the non-selective catalytic reduction catalyst element, the one or more reagent gases comprise one or more reductant gases and one or more oxidant gases, and the test gas flowing into the catalyst element has a $\lambda$ value of 1 or less including oxygen present in the test gas, wherein the cross sectional area of the gas inlet is less than the cross sectional area of the gas outlet.

18. The system of claim 17, wherein the reductant gas comprises carbon monoxide, gaseous aliphatic hydrocarbons, gaseous olefinic hydrocarbons, hydrogen, or mixtures thereof.

19. The system of claim 17, wherein the oxidant gas comprises nitric oxide, nitrogen dioxide, oxygen, or mixtures thereof.

20. The system of claim 17, wherein the system further comprises a gas controller that provides a predetermined quantity of the reagent gas to the carrier gas flowing through the system.

21. The system of claim 17, wherein the system further comprises a heater that heats the carrier gas flowing through the system.

22. The system of claim 17, wherein the gas inlet has a diameter less than a dimension of the catalyst element such that the gas inlet seals against a portion of the upstream surface of the catalyst element, and the gas outlet has a diameter less than a dimension of the catalyst element such that the gas outlet seals against a portion of the downstream surface of the catalyst element.

23. The system of claim 17, wherein the carrier gas flowing through the system for a $\lambda$ value greater than 1 comprises air.

24. The system of claim 17, wherein the carrier gas flowing through the system for a $\lambda$ value of 1 or less comprises an inert gas.

25. The system of claim 24, wherein the test gas further comprises water vapor.

26. The system of claim 17, wherein the test gas flowing through the gas flow path for a $\lambda$ value of 1 or less contains oxygen.

* * * * *